(12) United States Patent
Underhill et al.

(10) Patent No.: US 8,936,782 B2
(45) Date of Patent: Jan. 20, 2015

(54) INTERFERON BETA AS ANTIBACTERIAL AGENTS

(71) Applicant: Cedars-Sinai Medical Center, Los Angeles, CA (US)

(72) Inventors: David M. Underhill, Tarzana, CA (US); George Y. Liu, Los Angeles, CA (US); Amber Kaplan, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 13/683,545

(22) Filed: Nov. 21, 2012

(65) Prior Publication Data

US 2013/0129679 A1    May 23, 2013

Related U.S. Application Data

(60) Provisional application No. 61/562,984, filed on Nov. 22, 2011.

(51) Int. Cl.
*A61K 38/21*  (2006.01)
*A01N 37/18*  (2006.01)
*C07K 14/565* (2006.01)

(52) U.S. Cl.
CPC ............. *A61K 38/215* (2013.01); *C07K 14/565* (2013.01)
USPC .............. 424/85.6; 514/2.3; 514/2.6; 514/2.7

(58) Field of Classification Search
None
See application file for complete search history.

(56) References Cited

U.S. PATENT DOCUMENTS

| 5,019,382 | A  | * | 5/1991  | Cummins, Jr. | 424/85.4 |
| 2008/0260690 | A1 | * | 10/2008 | De Luca | 424/85.6 |
| 2009/0074712 | A1 | * | 3/2009  | Frith | 424/85.2 |
| 2009/0191154 | A1 | * | 7/2009  | Gillies et al. | 424/85.6 |

* cited by examiner

*Primary Examiner* — Christine J Saoud
*Assistant Examiner* — Jegatheesan Seharaseyon
(74) *Attorney, Agent, or Firm* — Linda B. Huber; Nixon Peabody LLP

(57) ABSTRACT

The present invention describes method of treating bacterial infections, including MRSA. In various embodiments, the methods can use interferon beta, which is found to have antimicrobial activity. In certain embodiments, the interferon beta can be human interferon beta. In other embodiments, the interferon beta can be mouse interferon beta. In further embodiments, the interferon beta can be human interferon beta containing amino acid substitutions to make the human interferon beta more cationic in neutral pH.

14 Claims, 7 Drawing Sheets

Fig. 3A

Mouse    SEQ. ID NO:1
N-ter
  1- I                                                          -1
  2- NYKQLQLQERTNIRKCQELLEQLNGKINLTYRADFKIPMEMTEKM               -46
 47- QKSYTAFAIQEMLQNVFLVFRNNFSSTGW                               -75
 76- NETIVVRLLDELHQQTVFLKTVLEEKQEERLTWEM                         -110
111- SSTALHLKSYYWRVQRYLKLMKY                                     -133
134- NSYAWMVVRAEIFRNFLIIRRLTRNFQN                                -161
     C-ter Human    SEQ. ID NO:2
N-ter
  1- MS                                                          -2
  3- YNLLGFLQRSSNFQCQKLLWQLNGRLEYCLKDRMNFDIPEEIKQLQQFQ            -51
 52- KEDAALTIYEMLQNIFAIFRQDSSSTGWN                                -80
 81- ETIVENLLANVYHQINHLKTVLEEKLEKEDFTRGKLMS                       -118
119- SLHLKRYYGRILHYLKAKEYS                                        -139
140- HCAWTIVRVEILRNFYFINRLTGYLRN                                  -166
C-ter

Fig. 3B

Muranized Human IFN-β

| Sequence | SEQ ID |
|---|---|
| Human [Mouse] ...IQEMLQNVFLVFRNNFSSTGWNETIVRLLDELHQQTVFLKTVLEEKQEERLTW--EMSSTALH... | SEQ. ID NO:3 |
| Mouse | SEQ. ID NO:4 |
| Mouse 1 ...FSSTGWNETIV[...]VRLLDELHQQTVFLKTVLEEKQEERLTW--EM... | SEQ. ID NO:5 |
| Mouse 2 ...[...]VRLLDELHQQTVFLKTVLEEKQEERLTW--EM... | SEQ. ID NO:6 |
| Mouse 3 ...[...]VRLLDELHQQTV[...]QEERLTW--EM... | SEQ. ID NO:7 |
| Mouse 4 ...[...]QEERLTW--EM... | SEQ. ID NO:8 |

Humanized Mouse IFN-β

| Sequence | SEQ ID |
|---|---|
| Mouse [Human] IQEMLQNVFLVFRNNFSSTGWNETIVRLLDELHQQTVFLKTVLEEKQEERLTW--EMSSTALH | SEQ. ID NO:4 |
| Human | SEQ. ID NO:3 |
| Mouse-Human 1 IQEMLQNVFLVFRNN[...]SSTALH | SEQ. ID NO:9 |
| Mouse-Human 2 IQEMLQNVFLVFRNNFSSTGWNETIV[...]SSTALH | SEQ. ID NO:10 |
| Mouse-Human 3 IQEMLQNVFLVFRNNFSSTGWNETIV[...]LKTVLEEKQEERLTW--EMSSTALH | SEQ. ID NO:11 |
| Mouse-Human 4 IQEMLQNVFLVFRNNFSSTGWNETIVRLLDELHQQTVFLKTVLEEK[...]SSTALH | SEQ. ID NO:12 |

INTERFERON BETA AS ANTIBACTERIAL AGENTS

STATEMENT REGARDING FEDERALLY-SPONSORED RESEARCH

The U.S. Government has a paid-up license in this invention and the right in limited circumstances to require the patent owner to license others on reasonable terms as provided for by the terms of Grant No. AI071116 awarded by the National Institutes of Health.

FIELD OF INVENTION

This invention relates to the treatment of bacterial infections with interferon-β

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

About two out of every 100 people carry a strain of staph that is resistant to antibiotics, also known as methicillin-resistant *Staphylococcus aureus* (MRSA). MRSA is tougher to treat than most strains of *staphylococcus aureus* due to its resistance to some commonly used antibiotics. Most often, it causes mild infections on the skin, causing sores or boils. But it can also cause more serious skin infections or infect surgical wounds, the bloodstream, the lungs, or the urinary tract. Though most MRSA infections are not serious, some can be life-threatening.

Bacteria rapidly evolve resistance to new antibiotics as they become widely used, and certain types of bacteria are becoming so resistant to standard antibiotics that treatment alternatives are dwindling. Thus, clinicians and industry are always looking for novel antimicrobial/antibacterial drugs. Accordingly, new treatment options are needed for these types of bacterial infections as well as other types of bacterial infections.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method for treating bacterial infection in a subject in need thereof, comprising: providing a composition comprising interferon-β (IFNβ); and administering the composition to the subject to treat the bacterial infection.

In various embodiments, the IFNβ can be mouse IFNβ, human IFNβ, recombinant IFNβ, or humanized mouse IFNβ. In various embodiments, the humanized mouse IFNβ can lower its ability to trigger IFNβ receptor signaling.

In various embodiments, the IFNβ can be IFNβ1. In various embodiments, the IFNβ1 can be mouse IFNβ1, human IFNβ1, recombinant IFNβ1, or humanized mouse IFNβ1. In various embodiments, the humanized mouse IFNβ1 can lower its ability to trigger IFNβ receptor signaling.

In various embodiments, the IFNβ1 can be IFNβ1a or IFNβ1b.

In various embodiments, the IFNβ1a can be mouse IFNβ1a, human IFNβ1a, recombinant IFNβ1a, or humanized mouse IFNβ1a. In various embodiments, the humanized mouse IFNβ1a can lower its ability to trigger IFNβ receptor signaling.

In various embodiments, the IFNβ1b can be mouse IFNβ1b, human IFNβ1b, recombinant IFNβ1b, or humanized mouse IFNβ1b. In various embodiments, the humanized mouse IFNβ1b can lower its ability to trigger IFNβ receptor signaling.

In various embodiments, the human IFNβ can be modified with one or more charged amino acids from the mouse structure to result in a more cationic IFNβ in a neutral pH environment.

Various embodiments of the present invention also provides a polypeptide having a mouse IFNβ sequence, wherein one or more amino acids from positions 76-98 of mouse IFNβ is replaced with a corresponding amino acid from human IFNβ.

Various embodiments of the present invention also provides a polypeptide having a human IFNβ sequence, wherein one or more amino acids from positions 76-98 of the human IFNβ sequence is replaced with a corresponding amino acid from a mouse IFNβ sequence.

These polypeptides can be used to treat bacterial infections according various methods of the present invention.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

FIG. 3 depicts an illustration of modifications to adjust the antimicrobial properties of human IFN-β. A) Amino acid sequence of mouse and human IFN-β showing in color the 5 helices of the structure. B) Illustration of strategies for making chimeric proteins that exchange regions of mouse IFN-β predicted to confer the antimicrobial activity of the protein at neutral pH compared to human IFN-β which is more active at acid pH. Muranized human IFN-β involves various combinations designed to move the 3rd helix (aa 76-98) and surrounding amino acids of mouse INF-β into the corresponding structural location of human IFN-β. Humanized mouse IFN-β involves doing the inverse.

DESCRIPTION OF THE INVENTION

Figure 1:
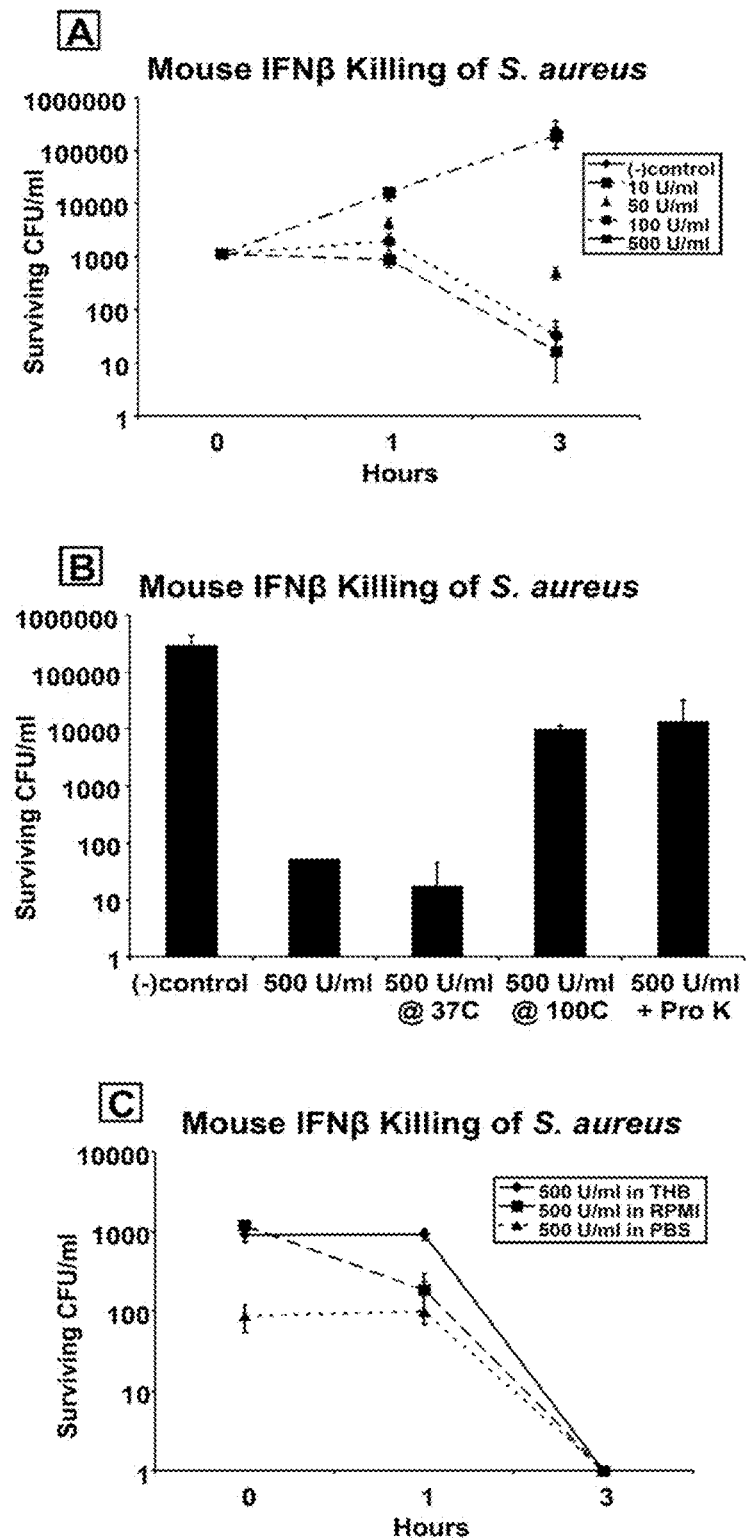
FIG. 1 depicts antimicrobial activities of mouse and human IFNβ in accordance with various embodiments of the present invention. A) Mouse interferon beta (IFNβ) dose curve showing antimicrobial activity against *Staphylococcus aureus*. B) Mouse IFNβ antimicrobial activity against *S. aureus* and treatments that inactivate killing: incubated at 37° C. for 1 hour, incubated at 100° C. for 1 hour, and treated with proteinase K for 1 hour. C) Mouse IFNβ antimicrobial activity against *S. aureus* at various growth stages. D) Mouse IFNβ antimicrobial activity against methicillin resistant *S. aureus* (MRSA), *Staphylococcus epidermis*, *Salmonella typhimurium*, and *Escherichia coli*. E) Mouse IFNβ has stronger antimicrobial activity against wild type *S. aureus* (Newman strain) than the isogenic DLT mutant. F) Human IFNβ has antimicrobial activity at lower pH.
Figure 1:
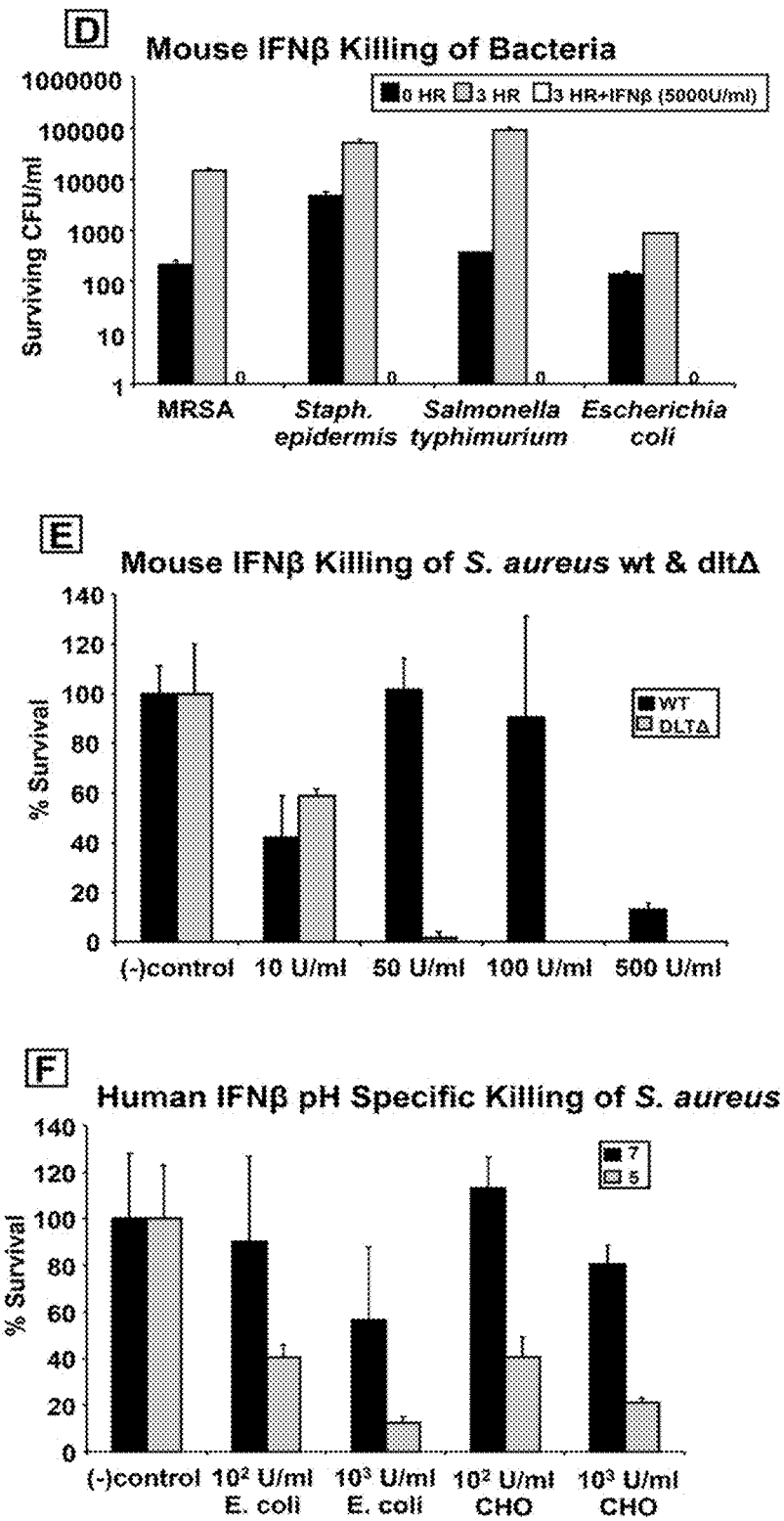
Figure 2:
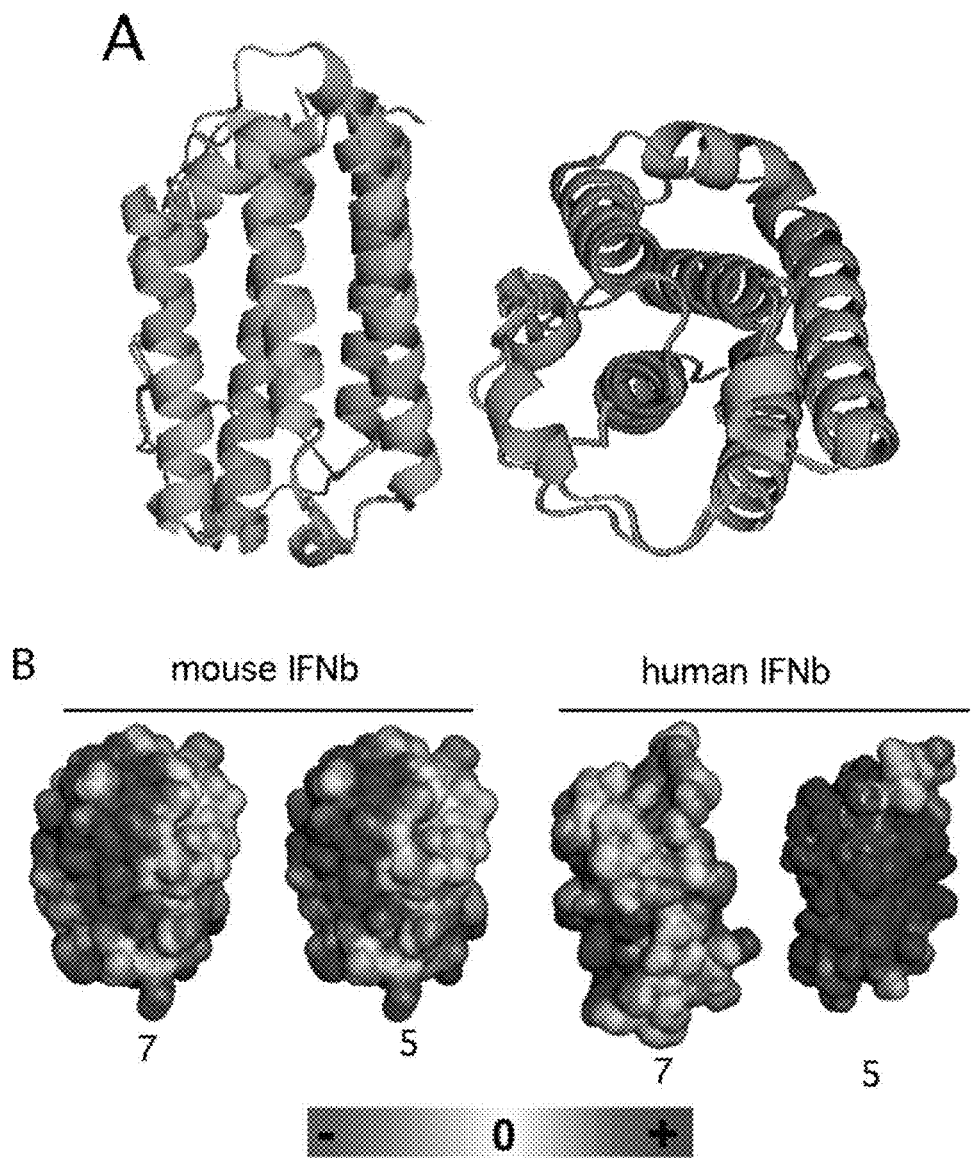
FIG. 2 depicts structural analysis of mouse and human IFNβ in accordance with various embodiments of the present invention. A) Overlay of mouse (blue) and human (green) IFNβ. Structural homology RMS=0.442. Disulphide bond in human but not mouse is shown in yellow. B) Electrostatic models showing mouse and human IFNβ residue charges under pH 7 and 5. Red residues are negatively charged, white are neutral, and blue are positive. Mouse IFNβ positive charges do not increase much at lower pH, however human IFNβ becomes much more positively charged at lower pH. C)-F) Q-Q plots showing charges at each residue for mouse and human IFNβ as well as mouse CXCL10 (a chemokine with antimicrobial properties) and mouse IL-6 (a cytokine with no antimicrobial properties). Blue peaks represent residues that become positively charged in lower pH. Human IFNβ has several residues in the C-terminus that become highly positively charged in lower pH.
Figure 2C:
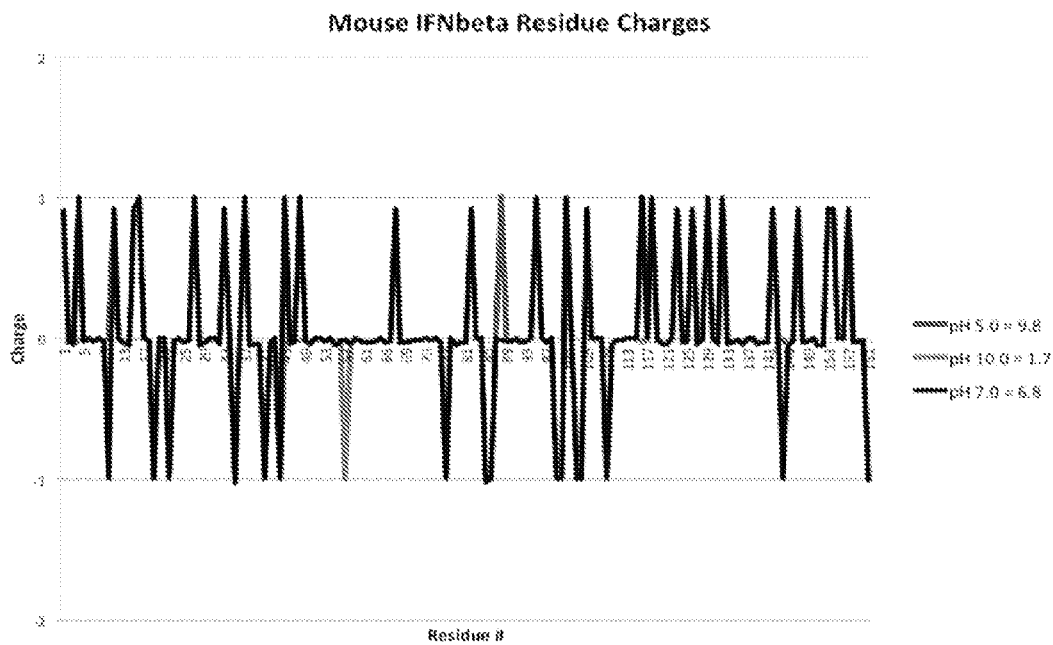
Figure 2D:
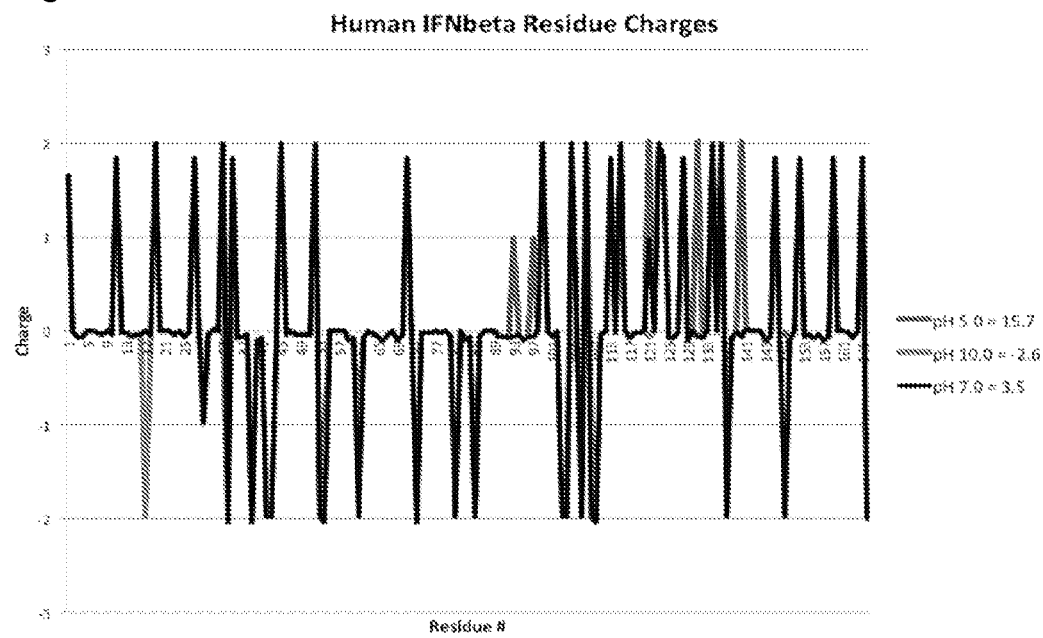
Figure 2E:
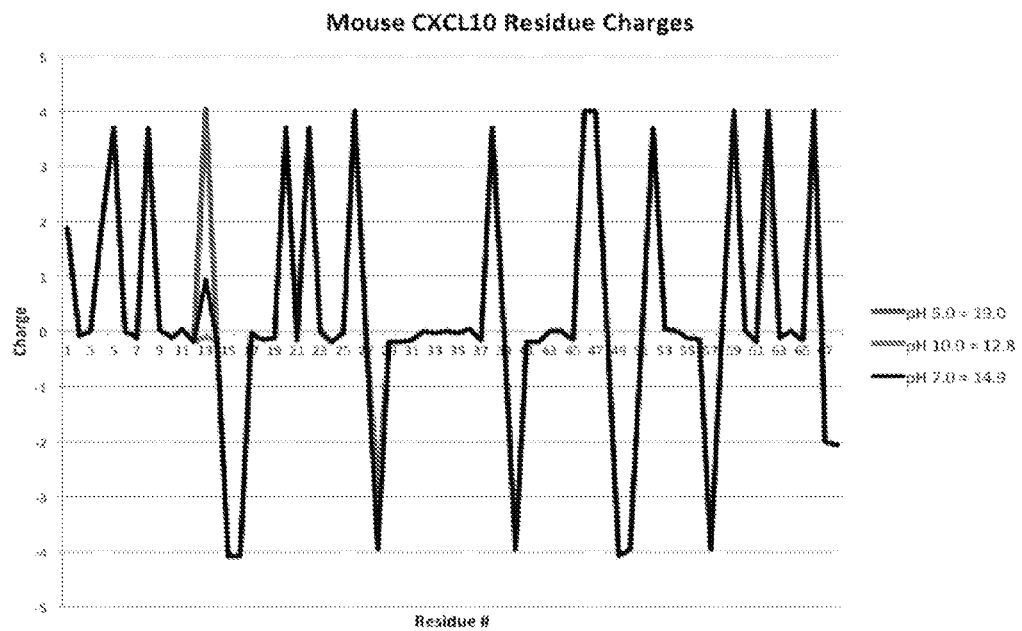
Figure 2F:
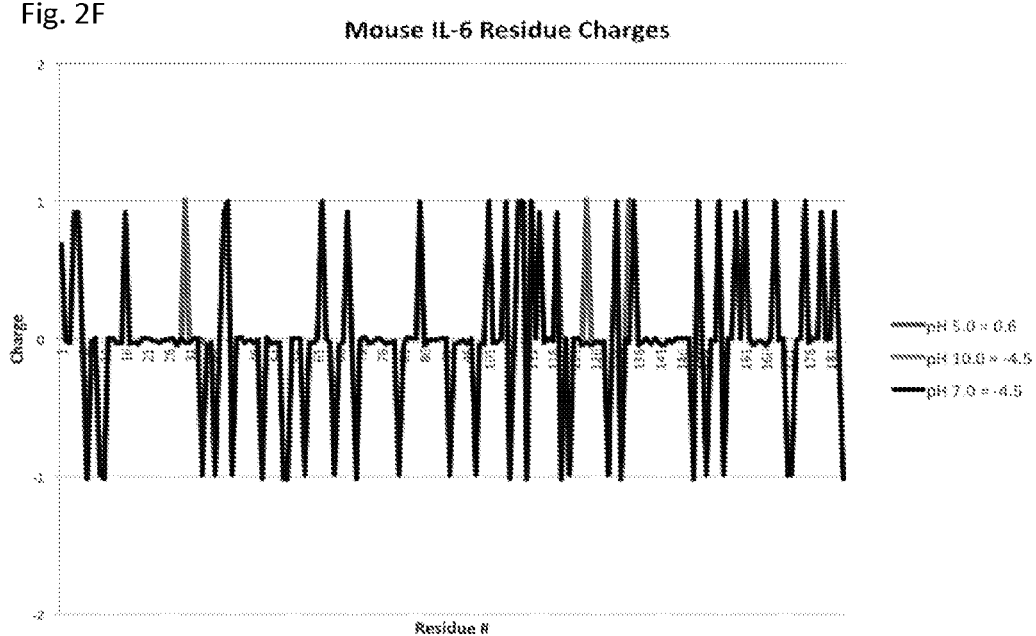

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

Interferon-β (IFNβ) is a cytokine in the interferon family. While initially discovered and investigated for its activity in stimulating cells to kill viruses, recombinant IFNβ has become a highly successful pharmaceutical used to treat multiple sclerosis (MS). How it helps in treating MS seems to be unknown. It is presumed that IFNβ activates immune cells for enhanced function. To this end, the receptor is known and much of its signaling activities have been described.

IFNβ has a previously unrecognized activity as an antibacterial peptide. Described herein are the inventors' findings of its antibacterial activity along with methods of treating bacterial infection.

The inventors discovered that in addition to its actions on cells through the IFNβ receptor, IFNβ has activity as an antimicrobial agent. This means that it has the ability to directly kill bacteria. It kills a wide range of Gram-positive and Gram-negative bacteria. At neutral pH, mouse IFNβ kills bacteria efficiently, while human IFNβ is not as efficient. Nonetheless, human IFNβ is still has antimicrobial activity at neutral pH. While not wishing to be bound to any particular theory, the inventors believe that this is due to a reduced positive charge on human IFNβ and that human IFNβ will work similarly to mouse at lower pHs. Indeed, human IFNβ has antimicrobial activity, and may be useful to acidic environments, such as but not limited to inside cells, and the mouse IFNβ structure can be used to design a more "murine-like" human IFNβ with greater activity at neutral pH. Further, it is known that human IFNβ can induce side effects due to activation of the IFNβ receptor and that mouse IFNβ does not activate the human receptor. Thus, mouse IFNβ or a "murine-like" human IFNβ could be used for its antimicrobial activity without stimulating receptor-driven side effects. Neutral pH refers to pH of 7.0, but can range from approximately 6.5-7.5 and still be considered as neutral. In various embodiments, neutral pH can range from approximately 6.6-7.4, 6.7-7.3, 6.8-7.2, or 6.9-7.1.

The inventors believe that IFNβ can be effective against antibiotic-resistant bacteria. The inventors have tested it against highly drug-resistant strains of *S. aureus* (MRSA) and found that IFNβ efficiently kills these bacteria.

As a multiple sclerosis (MS) therapy, recombinant IFNβ is injected subcutaneously at a dose of millions of international units per injection. At this dosage, antimicrobial concentrations (orders of magnitude lower) are easily achieved locally and systemic levels of IFNβ approach antimicrobial levels. Therefore, this is not an activity that appears only at an arbitrarily high and unphysiological dose.

Various embodiments of the present invention provide for a method of treating a bacterial infection in a subject in need thereof. The method can comprise providing a composition comprising IFNβ; and administering the composition to the subject in need thereof.

In various embodiments, the IFNβ is mouse IFNβ. In certain embodiments, the IFNβ is human IFNβ. In certain embodiments, the IFNβ is humanized mouse IFNβ. In various embodiments, the humanized mouse IFNβ lowers its ability to trigger IFNβ receptor signaling. In various embodiments, the human IFNβ is structure-based modified to make it more murine-like to enhance its antimicrobial activity. In certain embodiments, the IFNβ is recombinant IFNβ.

In various embodiments, the IFNβ is IFNβ1. In certain embodiments, IFNβ1 is mouse IFNβ1. In certain embodiments, the IFNβ1 is human IFNβ1. In certain embodiments, the IFNβ1 is humanized mouse IFNβ1. In various embodiments, the humanized mouse IFNβ1 lowers its ability to trigger IFNβ receptor signaling. In various embodiments, the human IFNβ1 is structure-based modified to make it more murine-like to enhance its antimicrobial activity. In certain embodiments, the IFNβ1 is recombinant IFNβ1.

In various embodiments, the IFNβ1 is IFNβ1a. In certain embodiments, IFNβ1a is mouse IFNβ1a. In certain embodiments, the IFNβ1a is human IFNβ1a. In certain embodiments, the IFNβ1a is humanized mouse IFNβ1a. In various embodiments, the humanized mouse IFNβ1a lowers its ability to trigger IFNβ receptor signaling. In various embodiments, the human IFNβ is structure-based modified to make it more murine-like to enhance its antimicrobial activity. In certain embodiments, the IFNβ1a is recombinant IFNβ1a.

In various embodiments, the IFNβ1 is IFNβ1b. In certain embodiments, IFNβ1b is mouse IFNβ1b. In certain embodiments, the IFNβ1b is human IFNβ1b. In certain embodiments, the IFNβ1b is humanized mouse IFNβ1b. In various embodiments, the humanized mouse IFNβ1b lowers its ability to trigger IFNβ receptor signaling. In various embodiments, the human IFNβ is structure-based modified to make it more murine-like to enhance its antimicrobial activity. In certain embodiments, the IFNβ1b is recombinant IFNβ1b.

IFNβ1a is available and is marketed as AVONEX (Biogen Idec), REBIF (Merck Serono); and IFNβ1b is available and is marketed as EXTAVIA (Novartis), and BETASERON (Bayer).

Modifications of human IFNβ, including but not limited to IFNβ1, IFNβ1a, and IFNβ1b, can be guided by the structure of mouse IFNβ. For example, human IFNβ can be modified with charged amino acids from the mouse structure so that it becomes more cationic in a neutral pH, similar to the mouse protein. As another example, human IFNβ can be modified as shown in FIG. 3B wherein regions involving the third helix (aa 76-98) and surrounding amino acids of mouse IFNβ are moved to the corresponding structural location of human IFNβ. In various embodiments, IFNβ is human IFNβ, wherein one or more amino acids from positions 76-98 of human IFNβ are replaced with the corresponding amino acid(s) from mouse IFNβ. In various embodiments, IFNβ is human IFNβ wherein 1, 2, 3, 4, 5, 6, 7, 8, 9, 10, 11, 12, 13, 14, 15, 16, 17, 18, 19, 20, 21, 22, or 23 amino acids or contiguous amino acids from positions 76-98 of human IFNβ are replaced with the corresponding amino acid(s) from mouse IFNβ.

Modifications of mouse IFNβ to produce a humanized mouse IFNβ, including but not limited to IFNβ1, IFNβ1a, and IFNβ1b, can also be done. For example, as shown in FIG. 3B, regions involving the third helix (aa 76-98) and surrounding amino acids of human IFNβ are moved to the corresponding structural location of mouse IFNβ. In various embodiments, IFNβ is mouse IFNβ, wherein one or more amino acids from positions 76-98 of mouse IFNβ are replaced with the corresponding amino acid(s) from human IFNβ. In various embodiments, IFNβ is mouse IFNβ wherein 1, 2, 3, 4, 5, 6, 7, 8, 9, 10, 11, 12, 13, 14, 15, 16, 17, 18, 19, 20, 21, 22, or 23 amino acids or contiguous amino acids from positions 76-98 of mouse IFNβ are replaced with the corresponding amino acid(s) from human IFNβ.

In various embodiments, the bacterial infection is resistant to at least one antibiotic. In certain embodiments, the bacterial infection is resistant to conventional antibiotics. In various embodiments, the bacterial infection is a MRSA infection. In various embodiments, the bacterial infection is caused by Gram-positive bacteria. In various embodiments, the bacterial infection is caused by Gram-negative bacteria. In various embodiments, the bacterial infection is *Staphylococcus epidermis* infection. In various embodiments, the bacterial infection is a *Salmonella typhimurium* infection. In various embodiments, the bacterial infection is an *Escherichia coli* infection. In various embodiments, the bacterial infection is a Group B *Streptococcus* infection.

In various embodiments, the present invention provide for pharmaceutical compositions including a pharmaceutically acceptable excipient along with a therapeutically effective amount of IFNβ as described herein. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to, topical, subcutaneous, intramuscular, systemic, aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection.

Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective IFNβ can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, such as biopsied infectious biological samples, or the responses observed in the appropriate animal models, as previously described. Examples of therapeutically effective dosages are millions of IU. As an example, injection (I.M.) of 6 million units of AVONEX once a week is common for M.S. patients and results in systemic serum levels of >50 u/ml (Khan & Dhib-Jalbut, Neurology 3:738), a concentration at which the mouse IFNβ has antibacterial activity at neutral pH and the human IFNβ has antibacterial activity at acidic pH. Accordingly, one or more injections of about 6 million units of IFNβ can be an effective dosage. As another example, a single injection of 16 million units of REBIF (s.c.) leads to serum levels >5 u/ml (FDA, REBIF documentation), a level that is close to its effective dose as an antibacterial. Accordingly, one or more injections of about 16 million units of IFNβ can be an effective dosage. In another example, for genital warts, IFNβ use has been tried with direct local injection into the affected tissue (at doses of up to millions of units/injection (Bonnez et al, J Infect Dis, 171:1081), and this dose is a large dose local for either human or mouse IFNβ. *Staphylococcus aureus*, for example, is a common skin infection with accessible lesions, and thus, this can be a therapeutically effective dosage and method. Accordingly, one or more local injections of one million units or more of IFNβ can be an effective dosage; for example, about two, three, four, five, six, seven, eight, nine, or ten million units. In yet another example, for genital warts, IFNβ has also been tried as a topical gel at doses from hundreds of thousands of units per gram to millions of units per gram. Again, these are large local doses and can have significant local antibacterial effects. Accordingly, one or more local injections of a hundred thousand units per gram to one million units per gram can be an effective dosage for topical administration. Accordingly, one or more topical administrations of a hundred thousand units per gram to one million units per gram can be an effective dosage. In further examples, an effective dosage can be 1, 2, 3, 4, 5, 6, 7, 8, 9, 10, 15, 20, 30, 40, 50, 75, 100, 200, 300, 400, 500, 600, 700, 800, or 900 thousand units or units per gram of the IFNβ. In further examples, an effective dosage can be 1, 2, 3, 4, 5, 6, 7, 8, 9, 10, 15, 20, 30, 40, 50, 75, 100, 200, 300, 400, 500, 600, 700, 800, or 900 million units or units per gram of the IFNβ.

The present invention is also directed to humanized mouse IFNβ, including but not limited to IFNβ1, IFNβ1a, and IFNβ1b. For example, as shown in FIG. 3B, regions involving the third helix (aa 76-98) and surrounding amino acids of human IFNβ are moved to the corresponding structural location of mouse IFNβ. In various embodiments, IFNβ is mouse IFNβ, wherein one or more amino acids from positions 76-98 of mouse IFNβ are replaced with the corresponding amino acid(s) from human IFNβ. In various embodiments, IFNβ is mouse IFNβ wherein 1, 2, 3, 4, 5, 6, 7, 8, 9, 10, 11, 12, 13, 14, 15, 16, 17, 18, 19, 20, 21, 22, or 23 amino acids or contiguous amino acids from positions 76-98 of mouse IFNβ are replaced with the corresponding amino acid(s) from human IFNβ.

Various embodiments of the present invention provide murinized human IFNβ, including but not limited to IFNβ1, IFNβ1a, and IFNβ1b. For example, human IFNβ can be modified with charged amino acids from the mouse structure so that it becomes more cationic in a neutral pH, similar to the mouse protein. As another example, human IFNβ can be modified as shown in FIG. 3B wherein regions involving the third helix (aa 76-98) and surrounding amino acids of mouse IFNβ are moved to the corresponding structural location of human IFNβ. In various embodiments, IFNβ is human IFNβ, wherein one or more amino acids from positions 76-98 of human IFNβ are replaced with the corresponding amino acid(s) from mouse IFNβ. In various embodiments, IFNβ is human IFNβ wherein 1, 2, 3, 4, 5, 6, 7, 8, 9, 10, 11, 12, 13, 14, 15, 16, 17, 18, 19, 20, 21, 22, or 23 amino acids or contiguous amino acids from positions 76-98 of human IFNβ are replaced with the corresponding amino acid(s) from mouse IFNβ.

The present invention is also directed to a kit to treat bacterial infections. The kit is useful for practicing the inventive method of treating bacterial infections. The kit is an assemblage of materials or components, including at least one of the inventive compositions. Thus, in some embodiments the kit contains a composition including IFNβ, as described above.

The exact nature of the components configured in the inventive kit depends on its intended purpose. For example, some embodiments are configured for the purpose of treating bacterial infections. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat bacterial infections. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

A patient presenting with MRSA infection is given an effective amount of IFNβ1a (AVONEX (Biogen Idec), REBIF (Merck Serono)) or IFNβ1b (EXTAVIA (Novartis), BETASERON (Bayer)) to treat the MRSA infection.

Example 2

A patient presenting with MRSA-infected skin lesions is given standard antibiotic therapy along with 3 times daily topical administration of gel containing $1 \times 10^6$ u/gm of IFNβ1a (AVONEX (Biogen Idec), REBIF (Merck Serono)) or IFNβ1b (EXTAVIA (Novartis), BETASERON (Bayer)).

Example 3

A patient presenting with a systemic MRSA infection is given standard antibiotic therapy along with weekly I.M. injection of $10 \times 10^6$ u/gm of IFNβ1a (AVONEX (Biogen Idec), REBIF (Merck Serono)) or IFNβ1b (EXTAVIA (Novartis), BETASERON (Bayer)) to achieve effective direct antimicrobial/antibacterial doses of the protein.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method for directly killing gram-positive bacteria in a subject in need thereof, comprising: providing a composition comprising interferon-β (IFNβ); and administering the composition to the subject in a dose sufficient to directly kill the gram-positive bacteria, wherein gram-positive bacteria is *S. aureus* or methicillin resistant *S. aureus* (MRSA) or *Staphylococcus epidermidis*.

2. The method of claim 1, wherein administering the composition comprises parenteral administration or transdermal administration.

3. The method of claim 1, wherein the gram-positive bacteria is *S. aureus*.

4. The method of claim 1, wherein the gram-positive bacteria is methicillin resistant *S. aureus* (MRSA).

5. The method of claim 1, wherein the gram-positive bacteria is *Staphylococcus epidermidis*.

6. The method of claim 1, wherein the IFNβ is mouse IFNβ.

7. The method of claim 1, wherein the IFNβ is human IFNβ.

8. The method of claim 1, wherein the IFβ1 is IFNβ1.

9. The method of claim 8, wherein the IFNβ1 is mouse IFNβ1.

10. The method of claim 8, wherein the IFNβ1 is human IFNβ1.

11. The method of claim 8, wherein the IFNβ1 is IFNβ1 a.

12. The method of claim 11, wherein the IFNβ1a is human IFNβ1a.

13. The method of claim 8, wherein the IFNβ1 is IFNβ1b.

14. The method of claim 13, wherein the IFNβ1b is human IFNβ1b.

* * * * *

SEQUENCE LISTING

```
<160> NUMBER OF SEQ ID NOS: 12

<210> SEQ ID NO 1
<211> LENGTH: 161
<212> TYPE: PRT
<213> ORGANISM: Murine

<400> SEQUENCE: 1

Ile Asn Tyr Lys Gln Leu Gln Leu Gln Glu Arg Thr Asn Ile Arg Lys
1               5                   10                  15

Cys Gln Glu Leu Leu Glu Gln Leu Asn Gly Lys Ile Asn Leu Thr Tyr
            20                  25                  30

Arg Ala Asp Phe Lys Ile Pro Met Glu Met Thr Glu Lys Met Gln Lys
        35                  40                  45

Ser Tyr Thr Ala Phe Ala Ile Gln Glu Met Leu Gln Asn Val Phe Leu
    50                  55                  60

Val Phe Arg Asn Asn Phe Ser Ser Thr Gly Trp Asn Glu Thr Ile Val
65                  70                  75                  80

Val Arg Leu Leu Asp Glu Leu His Gln Gln Thr Val Phe Leu Lys Thr
                85                  90                  95

Val Leu Glu Glu Lys Gln Glu Glu Arg Leu Thr Trp Glu Met Ser Ser
            100                 105                 110

Thr Ala Leu His Leu Lys Ser Tyr Tyr Trp Arg Val Gln Arg Tyr Leu
```

```
                115                 120                 125
Lys Leu Met Lys Tyr Asn Ser Tyr Ala Trp Met Val Val Arg Ala Glu
        130                 135                 140

Ile Phe Arg Asn Phe Leu Ile Ile Arg Arg Leu Thr Arg Asn Phe Gln
145                 150                 155                 160

Asn

<210> SEQ ID NO 2
<211> LENGTH: 166
<212> TYPE: PRT
<213> ORGANISM: Homo sapiens

<400> SEQUENCE: 2

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 3
<211> LENGTH: 65
<212> TYPE: PRT
<213> ORGANISM: Homo sapiens

<400> SEQUENCE: 3

Ile Tyr Glu Met Leu Gln Asn Ile Phe Ala Ile Phe Arg Gln Asp Ser
1               5                   10                  15

Ser Ser Thr Gly Trp Asn Glu Thr Ile Val Glu Asn Leu Leu Ala Asn
            20                  25                  30

Val Tyr His Gln Ile Asn His Leu Lys Thr Val Leu Glu Glu Lys Leu
        35                  40                  45

Glu Lys Glu Asp Phe Thr Arg Gly Lys Leu Met Ser Ser Leu His Leu
    50                  55                  60

Lys
65

<210> SEQ ID NO 4
<211> LENGTH: 62
<212> TYPE: PRT
<213> ORGANISM: Murine
```

-continued

<400> SEQUENCE: 4

Ile Gln Glu Met Leu Gln Asn Val Phe Leu Val Phe Arg Asn Asn Phe
1               5                   10                  15

Ser Ser Thr Gly Trp Asn Glu Thr Ile Val Val Arg Leu Leu Asp Glu
            20                  25                  30

Leu His Gln Gln Thr Val Phe Leu Lys Thr Val Leu Glu Glu Lys Gln
        35                  40                  45

Glu Glu Arg Leu Thr Trp Glu Met Ser Ser Thr Ala Leu His
    50                  55                  60

<210> SEQ ID NO 5
<211> LENGTH: 63
<212> TYPE: PRT
<213> ORGANISM: Artificial Sequence
<220> FEATURE:
<223> OTHER INFORMATION: synthetic construct

<400> SEQUENCE: 5

Ile Tyr Glu Met Leu Gln Asn Ile Phe Ala Ile Phe Arg Gln Asp Phe
1               5                   10                  15

Ser Ser Thr Gly Trp Asn Glu Thr Ile Val Val Arg Leu Leu Asp Glu
            20                  25                  30

Leu His Gln Gln Thr Val Phe Leu Lys Thr Val Leu Glu Glu Lys Gln
        35                  40                  45

Glu Glu Arg Leu Thr Trp Glu Met Met Ser Ser Leu His Leu Lys
    50                  55                  60

<210> SEQ ID NO 6
<211> LENGTH: 63
<212> TYPE: PRT
<213> ORGANISM: Artificial Sequence
<220> FEATURE:
<223> OTHER INFORMATION: synthetic construct

<400> SEQUENCE: 6

Ile Tyr Glu Met Leu Gln Asn Ile Phe Ala Ile Phe Arg Gln Asp Ser
1               5                   10                  15

Ser Ser Thr Gly Trp Asn Glu Thr Ile Val Val Arg Leu Leu Asp Glu
            20                  25                  30

Leu His Gln Gln Thr Val Phe Leu Lys Thr Val Leu Glu Glu Lys Gln
        35                  40                  45

Glu Glu Arg Leu Thr Trp Glu Met Met Ser Ser Leu His Leu Lys
    50                  55                  60

<210> SEQ ID NO 7
<211> LENGTH: 65
<212> TYPE: PRT
<213> ORGANISM: Artificial Sequence
<220> FEATURE:
<223> OTHER INFORMATION: synthetic construct

<400> SEQUENCE: 7

Ile Tyr Glu Met Leu Gln Asn Ile Phe Ala Ile Phe Arg Gln Asp Ser
1               5                   10                  15

Ser Ser Thr Gly Trp Asn Glu Thr Ile Val Val Arg Leu Leu Asp Glu
            20                  25                  30

Leu His Gln Gln Thr Val His Leu Lys Thr Val Leu Glu Glu Lys Leu
        35                  40                  45

Glu Lys Glu Asp Phe Thr Arg Gly Lys Leu Met Ser Ser Leu His Leu

```
                50                  55                  60
Lys
 65

<210> SEQ ID NO 8
<211> LENGTH: 63
<212> TYPE: PRT
<213> ORGANISM: Artificial Sequence
<220> FEATURE:
<223> OTHER INFORMATION: synthetic construct

<400> SEQUENCE: 8

Ile Tyr Glu Met Leu Gln Asn Ile Phe Ala Ile Phe Arg Gln Asp Ser
 1               5                  10                  15

Ser Ser Thr Gly Trp Asn Glu Thr Ile Val Glu Asn Leu Leu Ala Asn
            20                  25                  30

Val Tyr His Gln Ile Asn His Leu Lys Thr Val Leu Glu Glu Lys Gln
        35                  40                  45

Glu Glu Arg Leu Thr Trp Glu Met Met Ser Ser Leu His Leu Lys
    50                  55                  60

<210> SEQ ID NO 9
<211> LENGTH: 64
<212> TYPE: PRT
<213> ORGANISM: Artificial Sequence
<220> FEATURE:
<223> OTHER INFORMATION: synthetic construct

<400> SEQUENCE: 9

Ile Gln Glu Met Leu Gln Asn Val Phe Leu Val Phe Arg Asn Asn Ser
 1               5                  10                  15

Ser Ser Thr Gly Trp Asn Glu Thr Ile Val Glu Asn Leu Leu Ala Asn
            20                  25                  30

Val Tyr His Gln Ile Asn His Leu Lys Thr Val Leu Glu Glu Lys Leu
        35                  40                  45

Glu Lys Glu Asp Phe Thr Arg Gly Lys Leu Ser Ser Thr Ala Leu His
    50                  55                  60

<210> SEQ ID NO 10
<211> LENGTH: 64
<212> TYPE: PRT
<213> ORGANISM: Artificial Sequence
<220> FEATURE:
<223> OTHER INFORMATION: synthetic construct

<400> SEQUENCE: 10

Ile Gln Glu Met Leu Gln Asn Val Phe Leu Val Phe Arg Asn Asn Phe
 1               5                  10                  15

Ser Ser Thr Gly Trp Asn Glu Thr Ile Val Glu Asn Leu Leu Ala Asn
            20                  25                  30

Val Tyr His Gln Ile Asn His Leu Lys Thr Val Leu Glu Glu Lys Leu
        35                  40                  45

Glu Lys Glu Asp Phe Thr Arg Gly Lys Leu Ser Ser Thr Ala Leu His
    50                  55                  60

<210> SEQ ID NO 11
<211> LENGTH: 62
<212> TYPE: PRT
<213> ORGANISM: Artificial Sequence
<220> FEATURE:
<223> OTHER INFORMATION: synthetic construct
```

```
<400> SEQUENCE: 11

Ile Gln Glu Met Leu Gln Asn Val Phe Leu Val Phe Arg Asn Asn Phe
1               5                   10                  15

Ser Ser Thr Gly Trp Asn Glu Thr Ile Val Glu Asn Leu Leu Ala Asn
                20                  25                  30

Val Tyr His Gln Ile Asn His Leu Lys Thr Val Leu Glu Glu Lys Gln
            35                  40                  45

Glu Glu Arg Leu Thr Trp Glu Met Ser Ser Thr Ala Leu His
        50                  55                  60

<210> SEQ ID NO 12
<211> LENGTH: 64
<212> TYPE: PRT
<213> ORGANISM: Artificial Sequence
<220> FEATURE:
<223> OTHER INFORMATION: synthetic construct

<400> SEQUENCE: 12

Ile Gln Glu Met Leu Gln Asn Val Phe Leu Val Phe Arg Asn Asn Phe
1               5                   10                  15

Ser Ser Thr Gly Trp Asn Glu Thr Ile Val Val Arg Leu Leu Asp Glu
                20                  25                  30

Leu His Gln Gln Thr Val Phe Leu Lys Thr Val Leu Glu Glu Lys Leu
            35                  40                  45

Glu Lys Glu Asp Phe Thr Arg Gly Lys Leu Ser Ser Thr Ala Leu His
        50                  55                  60
```